(12) United States Patent
Michot et al.

(10) Patent No.: US 7,378,194 B2
(45) Date of Patent: May 27, 2008

(54) MATERIALS USEFUL AS ELECTROLYTIC SOLUTES

(75) Inventors: Christophe Michot, Grenoble (FR); Michel Armand, Montreal (CA); Michel Gauthier, La Prairie (CA); Nathalie Ravet, Montreal (CA)

(73) Assignees: ACEP, Inc. (CA); Centre de la Recherche Scientifique (CA); Universite de Montreal (CA)

( * ) Notice: Subject to any disclaimer, the term of this patent is extended or adjusted under 35 U.S.C. 154(b) by 64 days.

(21) Appl. No.: 10/954,487

(22) Filed: Oct. 1, 2004

(65) Prior Publication Data
US 2005/0084763 A1 Apr. 21, 2005

Related U.S. Application Data

(60) Division of application No. 09/986,681, filed on Nov. 9, 2001, now Pat. No. 6,841,304, which is a continuation of application No. 09/390,642, filed on Sep. 7, 1999, now Pat. No. 6,365,301.

(30) Foreign Application Priority Data

| Feb. 3, 1998 | (CA) | .................... 2228801 |
| Dec. 18, 1998 | (CA) | .................... 2256945 |
| Feb. 3, 1999 | (WO) | ............... PCT/CA99/00087 |

(51) Int. Cl.
*H01M 10/36* (2006.01)
*H01M 10/40* (2006.01)
*C01B 25/00* (2006.01)
*C07F 9/02* (2006.01)
*C07C 23/00* (2006.01)

(52) U.S. Cl. ............... 429/324; 429/307; 423/301; 423/302; 423/386; 423/387; 568/9; 568/11; 568/13; 568/16; 568/36; 568/557; 570/141; 570/142

(58) Field of Classification Search ............... 429/307, 429/315, 324; 423/301, 302, 386, 387; 359/270; 568/9, 11, 13, 16, 17, 36, 557; 570/141, 570/142; 361/505, 525
See application file for complete search history.

(56) References Cited

U.S. PATENT DOCUMENTS

| 4,256,379 A | 3/1981 | Green .................... 350/357 |
| 4,505,997 A | 3/1985 | Armand et al. ............. 429/192 |
| 5,256,821 A | 10/1993 | Armand ....................... 564/82 |
| 5,276,547 A | 1/1994 | Couput et al. ............... 359/270 |
| 5,350,646 A | 9/1994 | Armand et al. ............. 429/192 |
| 5,538,812 A | 7/1996 | Lee et al. ................... 429/192 |
| 5,737,114 A | 4/1998 | Bailey ........................ 359/268 |
| 5,916,475 A | 6/1999 | Michot et al. ............. 252/62.2 |
| 6,063,522 A | 5/2000 | Hamrock et al. ........... 429/200 |
| 6,254,797 B1 | 7/2001 | Michot et al. ............. 252/62.2 |
| 6,280,883 B1 | 8/2001 | Lamanna et al. ........... 429/307 |
| 6,350,545 B2 | 2/2002 | Fanta et al. ................. 429/307 |
| 6,365,301 B1 * | 4/2002 | Michot et al. ............. 429/307 |

FOREIGN PATENT DOCUMENTS

EP 0 834 892 A2 8/1998

OTHER PUBLICATIONS

Darstellung und Reaktionen des 1,2,3,5-Dithiadiazoliumchlorids, H.W. Roesky, et al. XP-002104842 (1978) Chem. Ber., vol. III, No. 8, month unknown.
Darstellung und Untersuchung von Fluorsulfurylverbindungen, H.W. Roesky, et al. XP-002104843 (1968) Chem. Ber., vol. I, No. 101, month unknown.
Chemistry of Imidobis(sulphuryl fluoride): Part II—Behaviour of Electrolytes in Imidobis(sulphuryl fluoride), P.L. Dhingra, et al., XP-002104844 Indian Journal of Chemistry, Jun. 1985.
Phosphor-und Schwefelhydrazin-Verbindungen, H.W. Roesky, et al. XP-002104845 (1971) Zeitschrift Fur Naturforschung, Teil B, vol. 26B, No. 12, pp. 1232-1235, month unknown.
Tetraphenylarsonium Bis(fluorosulfonyl)amide at 290 and 112 K, W. Isenberg, et al. XP-002104846 Acta Crystalographica, vol. B38, No. 11, pp. 2887-2889, Oct. 1982.
Preparation and Reactions of fluorosulfonyliminosulfuroxy Difluoride, H.W. Roesky, et al. XP-002104847 Inorganic Chemistry, vol. 8, No. 8, pp. 1733-1735, Aug. 1969.

* cited by examiner

*Primary Examiner*—Stephen J. Kalafut
(74) *Attorney, Agent, or Firm*—Katten Muchin Rosenman LLP

(57) ABSTRACT

The invention concerns novel ionic compounds with low melting point whereof the onium type cation having at least a heteroatom such as N, O, S or P bearing the positive charge and whereof the anion includes, wholly or partially, at least an ion imidide such as $(FX^1O)N^-(OX^2F)$ wherein $X^1$ and $X^2$ are identical or different and comprise SO or PF, and their use as solvent in electrochemical devices. Said composition comprises a salt wherein the anionic charge is delocalised, and can be used, inter alia, as electrolyte.

8 Claims, No Drawings

MATERIALS USEFUL AS ELECTROLYTIC SOLUTES

This is a divisional application of application Ser. No. 09/986,681, filed Nov. 9, 2001, now U.S. Pat. No. 6,841,304, issued Jan. 11, 2005 which is a continuation of application Ser. No. 09/390,642, filed Sep. 7, 1999 (now U.S. Pat. No. 6,365,301, issued Apr. 2, 2002). The entire text of each of the above-referenced disclosures is specifically incorporated by reference herein without disclaimer.

FIELD OF INVENTION

The present invention relates to ionic compositions having a high ionic conductivity, comprising a salt wherein the anionic charge is delocalized, and their uses, such as an electrolyte.

BACKGROUND OF THE INVENTION

Room temperature molten salts, such as triethyl ammonium nitrate, have been known for a long time. This product is of no interest except because of the presence of a leaving proton on the cation, limiting the redux or acido-basic stability domain of the compound. Methyl-ethylimidazolium or butyl-pyridinium type compounds, associated to the complex ion [Cl⁻, xAlCl₃] wherein 1<x<2, are also known. These compounds, because of the presence of the aluminium chloride, are powerful Lewis acids, hygroscopic and corrosive because they generate hydrochloric acid in the presence of humidity. Their electrochemical stability domain is also limited by the anodic oxydation of the chloride ion on one side, and by the reduction of the aluminium ion on the other side.

The use of anions usually stables associated to imidazolium or pyridinium type cations has been proposed, but the melting points are relatively high. For example, 1-methyl-3-ethylimidazolium hexafluorophosphate melts at 60° C., and 1,2-dimethyl-3-propylimidazolium hexafluorophosphate melts at 65° C. In addition, these salts, although not hygroscopic, are nevertheless soluble in water and can therefore be hardly prepared by ion exchange in water unless longer alkyl substituents are used, which results in a strong reduction in conductivity and enhanced viscosity.

U.S. Pat. No. 5,827,602 describes salts with a melting point relatively low, with a selection criteria being an anion volume higher than 100 Å$^3$, thus allowing to obtain salts with high conductivity and hydrophobic character. Most representative anions are the bis-trifluoromethanesulfonimidide, that has a calculated volume of 144 Å$^3$ with Hyperchem® program, or the tris-trifluoromethanesulfonylmethylide, which has a volume of 206 Å$^3$.

SUMMARY OF THE INVENTION

The present invention is concerned with low melting point ionic compounds, preferably lower than room temperature, wherein the cation is of the onium type and having at least one heteroatom such as N, O, S or P bearing the positive charge and wherein the anion comprises, in whole or in part, at least one imidide ion of the type $(FX^1O)N^-(OX^2F)$ wherein $X^1$ and $X^2$ are the same or different and comprise SO or PF. More specifically, the onium type cation comprises a compound of formula:

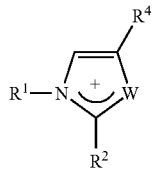

a compound of formula

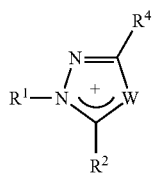

a compound of formula

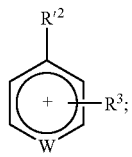

a compound of formula

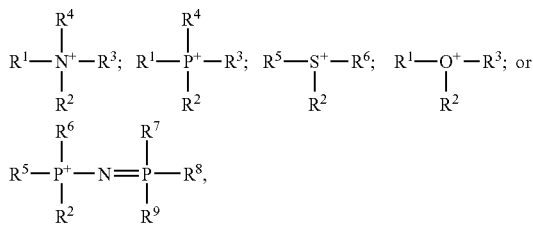

wherein

W is O, S or N, and wherein N is optionally substituted with $R^1$ when the valence allows it;

$R^1$, $R^3$, $R^4$ are the same or different and represent H;

an alkyl, alkenyl, oxaalkyl, oxaalkenyl, azaalkyl, azaalkenyl, thiaalkyl, thiaalkenyl, dialkylazo, each of these can be either linear, branched or cyclic and comprising from 1 to 18 carbon atoms;

cyclic or heterocyclic aliphatic radicals of from 4 to 26 carbon atoms optionally comprising at least one lateral chain comprising one or more heteroatoms;

groups comprising several aromatic or heterocyclic nuclei, condensed or not, optionally comprising one or more atoms of nitrogen, oxygen, sulfur or phosphorous; and wherein two groups $R^1$, $R^3$ or $R^4$ can form a cycle or a heterocycle of from 4 to 9 carbon atoms, and wherein one or more $R^1$, $R^3$ or $R^4$ groups on the same cation can be part of a polymeric chain;

$R^2$ and $R^5$ to $R^9$ are the same or different and represent $R^1$, $R^1O$—, $(R^1)_2N$—, $R^1S$—, $R^1$ being as defined above.

The invention further comprises an electrolytic composition comprising at least one ionic compound as defined above in combination with at least another component comprising a metallic salt, a polar polymer and/or an aprotic co-solvent.

DETAILED DESCRIPTION OF THE INVENTION

It has been found that onium-type cation salts as defined above, and preferably the imidazolium, ammonium, sulfonium and phosphonium salts, associated to anions of the family represented by the general formula $(FX^1O)N^-(OX^2F)$ as defined above allow to obtain liquid salts at temperatures equal or lower than those obtained with larger ions. Further, their conductivity is, in all instances, at the same temperature, superior to that of the compounds described in U.S. Pat. No. 5,827,602. These liquid salts are hydrophobic even though the anion size is small, comprised between 85 and 92 $Å^3$, and thus, easily prepared by ion exchange in water, and can be handled without any particular precaution. Unexpectedly, these salts show an oxydation stability equal to that of the bis(trifuoromethanesulfonimidide) or tris(trifluoromethanesulfonyl)methylide anions, and higher than that obtained with anions of the tetrafluoroborate or hexafluorophoborate type.

The compounds of the present invention can, in addition to the imidide anion mentioned above, comprise at least another anion selected from Cl$^-$; Br$^-$; I$^-$; NO$_3^-$; M(R$^{10}$)$_4^-$ A(R$^{10}$)$_6^-$; R$^{11}$O$_2^-$, [R$^{11}$ONZ$^1$]$^-$, [R$^{11}$YOCZ$^2$Z$^3$]$^-$, 4,5-dicyano-1,2,3-triazole, 3,5-bis(R$_F$)-1,2,4-triazole, tricyanomethane, pentacyanocyclopentadiene, pentakis-(trifluoromethyl)cyclopentadiene, barbituric acid and Meldrum acid derivatives and their substitution products;

M is B, Al, Ga or Bi;

A is P, As and Sb;

R$^{10}$ is a halogen;

R$^{11}$ represents H, F, allkyl, alkenyl, aryl, arylalkyl, alkylaryl, arylalkenyl, alkenylaryl, dialkylamino, alkoxy or thioalkoxy, each having from 1 to 18 carbon atoms and being unsubstituted or substituted with one or more oxa, thia, or aza substituents, and wherein one or more hydrogen atoms are optionally replaced with halogen in a ratio of 0 to 100%, and eventually being part of polymeric chain;

Y represents C, SO, S=NCN, S=C(CN)$_2$, POR$^{11}$, P(NCN)R$^{11}$, P(C(CN)$_2$R$^{11}$, an alkyl, alkenyl, aryl, arylalkyl, alkylaryl, arylalkenyl, alkenylaryl having from 1 to 18 carbon atoms and optionally substituted by one or more oxa, thia or aza; a dialk-ylamino group N(R$^{10}$)$_2$;

Z$^1$ to Z$^3$ representing independently R$^{11}$, R$^{11}$YO or CN, this group being optionally part of a polymeric chain.

Another advantage of the compounds of the invention is the low cost of the starting anions, their preparation not requiring perfluoroalkyl chemistry such as CF$_3$ or C$_4$F$_9$ for instance, the fluorine atoms present in the compounds of the invention being derived from inorganic chemistry products, thus easily accessible. This economical aspect is particularly important because the molten salts contain between 40 and 75% by weight of the anionic species, the remainder being the cationic species. In addition, the density of these liquids is close to 1.5, compared to about 1 for the organic solutions, which requires more important quantities of salts for all applications wherein a volume or a given thickness are necessary, such as electrolyte films, chemical reactors, etc.

Another particularly important aspect of the present invention is the possibility for these molten salts to dissolve other salts, in particular metallic salts, such as lithium salts, to give highly conductive solutions. In a similar manner, the molten salts, or their mixtures with other metallic salts, are excellent solvents or plasticizers for a great number of polymers, in particular those bearing polar or ionic functions. Liquid compounds as well as polymers plasticized by ionic mixtures behaving like solid electrolytes are applicable in electrochemistry to generators of the primary or secondary type, supercapacities, electrochromic systems, antistatic coatings, or electroluminescent diodes. The non-volatility of the molten salts of the invention, their thermal and electrochemical stability, and their enhanced conductivity are important parameters for the fabrication of devices working at low temperature and not presenting the usual flammability risks associated with the use of conventional organic solvents.

The molten salts of the invention are polar media of low volatility, and because of this, are capable of being used as solvents to perform a great number of organic chemistry reactions, such as nucleophilic an electrophilic substitutions, or anionic, cationic or radicalar polymerisations. It is also possible to dissolve catalysts in such media, in particular transition metal salts or rare earth salts eventually coordinated with ligands, to increase the catalytic properties. Examples of such catalysts include bipyridines, porphyrines, phosphines, arsines. Organometallics like metallocenes are also included as solutes that can present catalytic properties.

The non-votatility of the molten salts, their thermal stability and their non-miscibility with non-polar solvents like hydrocarbons, as well as their hydrophobic character, are particularly advantageous to separate the chemical reaction products. It is also possible to work in diphasic systems, the molten salts containing the catalyst and the reacting substrates being in solution in a hydrocarbon or non-miscible aliphatic ether. After the reaction, a simple decantation can separate the organic phase containing the reaction product and the molten salt that is purified by washing with a non-solvent such as water or hydrocarbon, and dried by simple in vacuo procedure.

The ammonium, phosphonium and sulfonium cations can have an optical isomery and the molten salts containing them are corral solvents susceptible or favoring the formation of enantiomeric excesses in the reactions performed in these media. Preferred cations for the present invention comprise the compounds of formula:

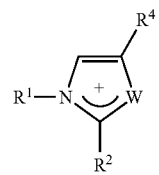

that include the imidazolium, triazolium, thiazolium, and oxazolium derivatives; the compounds of formula

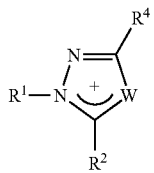

that include the trizolium, oxadiazolium, and thadiazolium; the compounds of formula

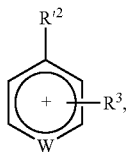

preferably pyridiium derivatives

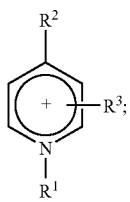

the compounds of formula

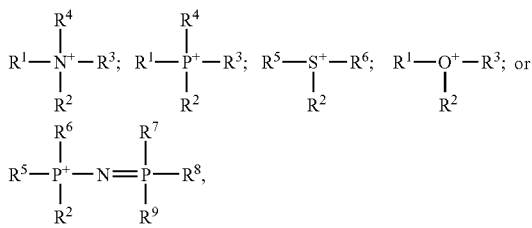

wherein

W is O, S or N, and wherein N is optionally substituted with $R^1$ when the valence allows it;

$R^1$, $R^3$, $R^4$ are the same or different and represent H;

an alkyl, alkenyl, oxaalkyl, oxaalkenyl, azaalkyl, azaalkenyl, thiaalkyl, thiaalkenyl, dialkylazo, each of these can be either linear branched or cyclic and comprising from 1 to 18 carbon atoms;

cyclic or heterocyclic aliphatic radicals of from 4 to 26 carbon atoms optionally comprising at least one lateral chain comprising one or more heteroatoms such as nitrogen, oxygen or sulfur;

aryl, arylalkyl, alkylaryl and alkenyaryl of from 5 to 26 carbon atoms optionally comprising one or more heteroatoms in the aromatic nucleus;

groups comprising several aromatic or heterocyclic nuclei, condensed or not, optionally comprising one or more atoms of nitrogen, oxygen, sulfur or phosphorous; and wherein two groups $R^1$, $R^3$ or $R^4$ can form a cycle or a heterocycle from 4 to 9 carbon atoms, and wherein one or more $R^1$, $R^3$ or $R^4$ groups on the same cation can be part of a polymeric chain;

$R^2$ and $R^5$ to $R^9$ are the same or different and represent $R^1$, $R^1O—$, $(R^1)_2N—$, $R^1S—$, $R^1$ being as defined above.

R1, R3 and R4 groups can bear groups active in polymerization such as double bonds or epoxides, or reactive functions in polycondensations, such as OH, NH2, or COOH. When the cations include double bonds, they can be homopolymerized or copolymerized, for instance with vinylidene fluoride, an acrylate, a maleimide, acrylonitrile, a vinylether, a styrene, etc. Epoxide groups can be polycondensed or copolymerized with other epoxides. These polycations are particularly useful alone or in a mixture with a solvent, including a molten salt of the present invention and/or one or more lithium salt or a mixture of lithium and potassium salts as electrolyte in lithium batteries with a lithium anode or using a cathode inserting the lithium at low potential such as titanium spinel or carbonated materials.

The invention further concerns an electrolytic composition comprising at least one ionic compound comprising at least one anion and at least one cation as defined above in combination with at least another compound comprising a metallic salt, a polar polymer and/or an aprotic co-solvent. A preferred cation of the metallic salt comprises the proton, an alkaline metal cation, an alkaline-earth metal cation, a transition metal cation, a rare earth metal cation, lithium being particularly preferred.

A preferred polar polymer comprises monomer units derived from ethylene oxide, propylene oxide, epichlorohydrine, epifluorohydrine, trifluoroepoxypropane, acrylonitrile, methacrylonitrile, esters and amides of acrylic and methacrylic acid, vinylidene fluoride, N-methylpyrrolidone and polyelectrolytes of the polycation or polyanion. Finally, examples of preferred aprotic co-solvent include di-alkylic ethers of ethylene glycol, diethylene glycol, triethylene glycol, polyethylene glycols of weight comprised between 400 and 2000; esters, in particular those of carbonic acid, linear or cyclics such as dimethylcarbonate, methyl-ethyl-carbonate, diethylcarbonate, ethylene carbonate, propylene carbonate; esters like γ-butyrolactone, nitrites like glutaronitrile, 1,2,6-tricyanohexane, amides such as dimethylformamide, N-methylpyrrolidinone, sulfamides and sulfonamides as well as mixtures thereof.

When the present electrolytic composition comprises more than one polymer, at least one of those can be cross-linked.

An electrochemical generator comprising an electrolytic composition of the present invention preferably comprises a negative electrode containing either lithium metal or an alloy thereof, or a carbon insertion compound, in particular petroleum coke or graphite, or a low potential insertion oxide such as titanium spinel $Li_{4-x+3y}Ti_{5-x}O_{12}$ ($0 \leq x, y \leq 1$), or a double nitride of a transition metal and lithium such as $Li_{3-x}Co_zN$ ($0 \leq z \leq 1$) or having a structure of the antifluorite type like $Li_3FeN_2$ or $Li_7MnN_4$, or mixtures thereof. The positive electrode of the generator preferably contains either vanadium oxide $VO_x$ ($2 \leq x \leq 2,5$), a mixed oxide of lithium and vanadium $LiV_3O_8$, a double oxide of cobalt and lithium optionally partially substituted of general formula $Li_{1-\alpha}Co_{1-x+y}Ni_xAl_y$ ($0 \leq x+y \leq 1$; $0 \leq y \leq 0,3$; $0 \leq \alpha \leq 1$), a manganese spinel optionally partially substituted of general formula $Li_{1-\alpha}Mn_{2-z}M_z$ ($0 \leq z \leq 1$) wherein M=Li, Mg, Al, Cr, Ni, Co, Cu, Ni, Fe; a double phosphate of the olivine or Nasicon structure such as $Li_{1-\alpha}Fe_{1-x}Mn_xPO_4$, $Li_{1-x+2\alpha}Fe_2P_{1-x}Si_xO_4$ ($0 \leq x$, $\alpha \leq 1$), a rhodizonic acid salt, a polydisulfide derived from the oxidation of dimercaptoethane, 2,5-dimercapto-1,3,4-thiadiazole, 2,5-dimercapto-1,3,4-oxadiazole, 1,2-dimercaptocyclobutene-3,4-dione, or mixtures thereof.

Advantageously, at least one of the electrodes of the generator is mixed with the electrolytic composition to form a composite electrode.

The electrolytic composition of the invention can also be used as an electrolyte in an electrical energy storage system of the supercapacity type, optionally containing, in an electrode, carbon with high specific surface, or a conjugated polymer. Advantageously, the conjugated polymer comprises 3 degrees of oxidation, and is found in both electrodes. An example of such a polymer is a derivative of phenyl-3-thiophene.

Finally, the electrolytic composition of the invention can be used as an electrolyte in a light modulating system of the electrochromic type comprising as least one electrochromic material. In such a system, the electrochromic material is advantageously deposited on a layer of a semi-conductor transparent in the visible, preferably a tin oxide or indium oxide derivative, on a glass or polymer substrate. Examples of preferred electrochomic materials include oxides of molybdenum, tungsten, titanium, vanadium, niobium, cerium, tin, and mixtures thereof. The electrochromic material can optionally be dissolved in the electrolyte.

The following examples are provided to illustrate preferred embodiments of the present invention, and should not be construed as limiting its scope.

EXAMPLE 1

15 g of 1-methyl-3-ethyl imidazolium chloride EMICl ($C_6H_{11}N_2Cl$) are dissolved in 100 ml of water to which are added 23 g of potassium bis-fluorosulfonimidide (KFSI) $K[(FSO_2)_2N]$. A separation in two liquid phases is immediately obtained. The molten salt of 1-methyl-3-ethyl imidazolium bis-fluorosulfonimidide (EMIFSI) is extracted with dichloromethane and dried with anhydrous magnesium sulfate. The suspension is filtered and the solvent evaporated. The salt is dried under vacuum at 80° C., and corresponds to the developed formula:

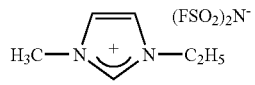

This ionic compound examined under DSC presents a melting point of −15° C. The weight loss measured by differential thermal analysis (DTA) under argon is lower than 1% up to 350° C. The conductivity and the function of the temperature are provided in Table 1 below.

TABLE 1

| | Temperature (° C.) | | | | | | | |
|---|---|---|---|---|---|---|---|---|
| | −10 | 0 | 10 | 20 | 30 | 40 | 50 | 60 |
| Conductivity ($mScm^{-1}$) | 5.6 | 8.3 | 11 | 15 | 20 | 25 | 31 | 37 |
| σ(FSI)/σTFSI (%) | 2.41 | 2.21 | 2.01 | 1.86 | 1.80 | 1.70 | 1.67 | 1.64 |

The conductivity: is higher than that obtained with the 1-methyl-3-ethyl imidazolium bis-trifluoromethanesulfonimidide salt (EMITFSI). The ratio between the conductivity values a between the salt of the invention, i.e., 1-methyl-3-ethyl imidazolium fluorosulfonimidide (noted FSI in the table) and 1-methyl-3-ethyl imidazolium bis-trifluoromethanesulfonimidide (noted TFSI in the table) is given in the last line of Table 1. These numbers show the significant improvement in the performances of the conductivity with respect to the prior art.

The electrochemical stability domain measured by cyclic voltammetry on a nickel electrode for cathodic potentials in vitreous carbon for anodic potentials is 5.2 Volts ($0 \Rightarrow 5.2$ V vs. $Li^+/Li^\circ$).

EXAMPLE 2

Lithium bis-difluorophosphonylamidide $Li[(POF_2)_2N]$ is prepared according to the method of Fluck and Beuerle in *Z. Anorg. Allg. Chem.*, 1975, 412, 65, by reacting the lithiated derivative of hexamethyldisilazane on phosphorus oxyfluoride according to the following reaction:

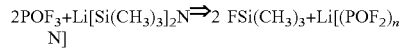

The molten ionic salt 1-methyl-3-ethyl imidazolium bis-difluorophosphonylimidide is prepared by ionic exchange in water according to Example 1 between 10 g of 1-methyl-3-ethyl imidazolium chloride and 13 g $Li[(POF_2)_2N]$ and extraction with dichloromethane. The molten salt has physical/chemical properties similar to that of the fluorosulfonyl of Example 1.

EXAMPLE 3

Different imidazolium salts of general formula:

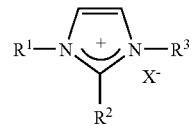

have been prepared with anions $[(FSO_2)_2N]^-$ and $[(POF_2)_2N]^-$, and are illustrated in Table 2 below. Those with the sign "+" are liquid salts at room temperature.

TABLE 2

| $R^3 =$ | $CH_3$ | $C_2H_5$ | $C_3H_7$ | $C_4H_9$ | $C_5H_{11}$ | $C_7H_{15}$ | $C_8H_{17}$ |
|---|---|---|---|---|---|---|---|
| $R^1 = CH_3$, $R^2 = H$ | | + | + | + | + | + | + |
| $R^1 = CH_3$, $R^2 = CH_3$ | | | + | + | + | + | + |
| $R^1 = C_2H_5$, $R^2 = H$ | + | + | + | + | + | + | + |
| $R^1 = CH_3$, $R^2 = C_3H_3$ | + | + | + | + | + | + | + |

EXAMPLE 4

10 g of commercial ammonium triethylhexyl bromide ($C_{12}H_{28}NBr$) are dissolved in 150 ml of water to which are added under agitation 8.5 g of potassium bisfluorosulfonimidide $[K(FSO_2)_2N]$. The molten salt triethylhexyl ammonium bis-fluorosulfonimidide is separated by centrifugation and washed with three aliquots of 50 ml of water and extracted with 30 ml of dichloromethane and dried with anhydrous magnesium sulfate. The suspension is filtered and the solvent evaporated, leaving a viscous liquid. The conductivity at 25° C. is higher than $5 \times 10^{-4}$ Scm$^{-1}$ at 25° C.

EXAMPLE 5

10 g of commercial dimethylethylamine and 11 ml of bromo-1-propane are refluxed in 40 ml of acetonitrile for 48 hours. The solvent is then evaporated and the solid residue is washed with ether. To 12 g of the salt $(CH_3)_2(C_2H_5)(C_3H_7)NBr$ dissolved in 75 ml of water are added 13 g of potassium bis-fluorosulfonimidide $[K(FSO_2)_2N]$. The molten salt is extracted as above to give a liquid of low viscosity. Its conductivity in view of various temperatures is provided in Table 3 below.

TABLE 3

|  |  | Temperature (° C.) | | | |
| --- | --- | --- | --- | --- | --- |
|  |  | 20 | 30 | 40 | 50 |
| Conductivity (mScm$^{-1}$) | FSI | 4.95 | 7.02 | 9.4 | 12.3 |
|  | TFSI | 1.81 | 2.92 | 4.3 | 6.1 |

For comparison purposes, the conductivity of the dimethylethylpropylammonium bis-trifluoromethanesulfonimidide salt is given (Table 3, line 3). The conductivity of the compound of the invention is from about 2.5 to 2 times higher than that of the equivalent salt having a bigger anion.

EXAMPLE 6

N-methyl-N-ethyl-aniline is quaternized by bromopropane under reflux in acetonitrile for 48 hours. The salt is obtained by evaporation of the solvent and purified by washing the solid residue with ether. 5 g of the salt obtained are dissolved in 25 ml of water, and 4.6 g of potassium bis-fluorosulfonimidide $(K(FSO_2)_2N)$ are added. The molten salt methylethylpropylphenyl ammonium bis-fluorosulfonimidide is extracted with 15 ml of dichloromethane, washed with three aliquots of 50 ml of water and dried with anhydrous magnesium sulfate. The salt exists under two optical isomers that can be separated on a corral column or by precipitation of the camphor-sulfonate salt with bromide before exchange with the imidide. The salt can be used in a corral reactional media.

EXAMPLE 7

N-butylpyridinium bromide is prepared by reacting bromobutane on pyridine in the absence of a solvent at 45° C. To 5 g of this salt dissolved in 35 ml of water are added 4.6 g of lithium bis-difluorophosphonylimidide $Li[(POF_2)_2N]$. The liquid salt is treated in a manner similar to that of the molten salt obtained in the above examples and is finally dried under vacuum at 60° C. The molten salt of N-propyl pyridinium bis-fluorosulfonimidide is prepared in a similar manner from the corresponding potassium salt.

EXAMPLE 8

Commercial ethylmethyl sulfide (Aldrich) is quaternized by propyl sulfate (TCI). Diethylmethylpropylsulfonium propylsulfate is treated in an aqueous solution with one equivalent of potassium bis-fluorosulfonimidide. The molten salt is extracted as above. In a manner similar to that described in Example 4, the salt can be separated into two optically active isomers and used to induce an enantiomeric excess for reactions performed when the salt is used as a solvent.

EXAMPLE 9

15 g of commercial 4-chloropyridine chlorhydrate are dissolved in 100 ml of water to which are added 8.5 g of sodium bicarbonate. The 4-chloropyridine is extracted with ether and dried with magnesium sulfate, and the solvent is evaporated. 10 g of 4-chloropyridine in 60 ml of acetonitrile are quaternized by 15.6 g of ethyl trifluoromethanesulfonate and 11.6 g of trimethylsilylethylmethyl-amine $C_2H_5(CH_3)NSi(CH_3)_3$ are added. The reaction medium is refluxed for an hour, then cooled. The solvent is evaporated and the solid residual is placed in water. To this solution are added 19.5 g of potassium bis-fluorosulfonimidide. The decanting liquid salt is extracted with dichloromethane. The salt has the following structure:

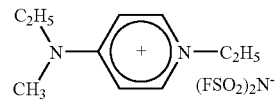

EXAMPLE 10

Fluorosulfonamide $FSO_2NH_2$ is prepared by reacting fluorosulfonic anhydride (15 g) with ammonium carbamate (12 g) in suspension in dichloromethane according to the following reaction:

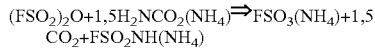

The reaction medium is filtered. The amide $FSO_2NH_2$ is freed by diluted hydrochloric acid and extracted with ether. The trimethylsilylated derivative of the sodic derivative of the fluorosulfonamide is prepared according to the method of Foropoulous et al. in *Inorganic Chem.*, 1984, 23, 3720. In a Parr® reactor, 80 ml of anhydrous acetonitrile are mixed with 10 g of the fluorosulfonamide derivative. The reactor is closed and purged under nitrogen, and 5.38 g of phosphoryl fluoride $POF_3$ are added while maintaining the temperature at 45° C. The pressure falls after an hour and the reactor is cooled and opened. The sodium salt of the mixed imide is obtained according to the reaction:

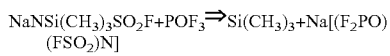

The salt is recovered by evaporation of the solvent and recrystallization in a toluene-acetonitrile mixture. This salt gives liquid ionic derivatives with the imidazolium of Example 3, and shows liquid domains wider than that of the bis-trifluoromethanesulfonimidide and a conductivity higher by 10 à 25%.

EXAMPLE 11

25 ml of a commercial solution of diallyldimethyl-ammonium chloride (65%) in water are diluted with 100 ml, and 22 g of potassium bis-fluorosulfonimidide are added under agitation. The liquid precipitate is extracted with dichloromethane and dried with magnesium sulfate. This molten salt has the following formula:

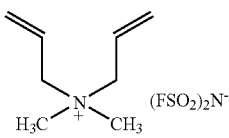

It behaves like a monomer active in radicalar polymerisation to form, through cyclopolymerization, dimethylpyrrolidinium bis(3,5-methylene-) patterns. This compound gives, in addition to homopolymers, copolymers with styrene, maleic anhydride, N-maleimides, vinylidene fluoride, acrylonitrile, methacrylonitrile, methyl methacrylate, acrylates or methacrylates of ω-methoxyoligo ethylene glycols of weight comprised between 200 and 2000 daltons, eventually cross-linked with a diacrylate or methacrylate of α, ω-oligo ethylene glycol.

EXAMPLE 12

5 g of phosphorous pentachloride are dissolved in 50 ml dichloromethane in a flask comprising a bromine funnel and a dry argon entrance. The mixture is cooled with dry ice at −78° C. and 20 ml of methylethylamine in 30 ml of anhydrous acetonitrile are added drop wise through the bromine funnel. The reaction medium is maintained under agitation for an hour until room temperature is reached. The solvent is then evaporated and the residue is washed with 75 ml of water and filtered on Celite®. To this solution are added 5.5 g of potassium bis-fluorosulfonimidide. The reaction medium separate into two liquid phases. The molten salt of tetrakis(ethylmethylamino)phosphonium {P[N(CH$_3$)(C$_2$H$_5$)]$_4$}$^-$[(FSO$_2$)$_2$N]$^-$ is an oily liquid at room temperature. This molten salt is particularly stable towards reducing or nucleophilic agents, even at high temperatures.

EXAMPLE 13

20 g of a commercial aqueous solution of 25% of poly(diallyldimethylammonium) chloride of high molecular weight (M$_w$ about 2×10$^5$) are diluted in 100 ml of water. Under magnetic agitation are added 6.7 g of potassium bis-fluorosulfonimidide in 100 ml of water. The precipitate of poly(diallyldimethylammonium bis-fluorosulfonimidide)

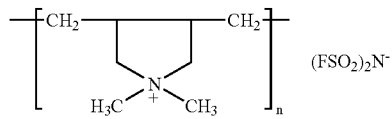

is then filtered and washed abundantly with distilled water, then dried under vacuum.

EXAMPLE 14

A liquid electrolyte is obtained by dissolving lithium bis-trifluoromethanesulfonylimidide (LiTFSI) in a 1 molar concentration in the molten salt prepared in Example 1. Conductivity of this mixture is 9×10$^{-3}$ Scm$^{-1}$ at 25° C., and remains higher than 2×10$^{-3}$ Scm$^{-1}$ at 0° C. The anodic domain found by cyclic voltammetry is superior to 5 V/Li°/Li$^+$.

EXAMPLE 15

A solid electrolyte is obtained by plasticization of the polyelectrolyte of Example 13 with a solution of the lithium salt in the imidazolium of Example 14. To mold this electrolyte, the 3 components. (polyelectrolyte-FSI, imidazolium-FSI, LiTFSI) are weighted according to the following ratios: polyelectrolyte (40% by weight); LiTFSI, 1 M in the imidazolium salt (60% by weight). The three components are dissolved in a volatile polar solvent, such as acetonitrile, the amount of solvent being adjusted to allow spreading of the solution as a thin film to give after drying a thickness of 35 μm on a polypropylene support.

The film thus obtained is dried by dry air, then placed under a primary vacuum at 100° C. for 2 hours. All further handling of this film are made in a glove box (<1 ppm O$_2$ and H$_2$O). The conductivity of this electrolyte is equal to 10$^{-3}$ Scm$^{-1}$ at 20° C.; 4×10$^{-4}$ Scm$^{-1}$ at 0° C.; and 3×10$^{-3}$ Scm$^{-1}$ at 60° C. Electrolytes with higher conductivity can be obtained by raising the fraction of the plasticizer (>60%), i.e., the solution of LiTFSI of the molten salt of Example 1. In a similar manner, higher elasticity modules are obtained for plasticizers fractions <50% with a reduction in conductivity.

EXAMPLE 16

A polymer electrolyte of high conductivity is obtained by plasticizing a metallic salt-polyether complex with 40% by weight of an anionic compound of Example 2. The complex comprises lithium bis-trifluoromethanesulfonimidide of poly(ethylene oxide) of molecular weight 5×10$^6$, in a manner such that the ratio of the oxygen atoms of the polymer versus the number of lithium ions is equal to 20 (O:Li=20:1). The electrolyte can be prepared directly by co-dissolving the components weighted according to the stoichiometric proportions in a solvent such as acetonitrile, and evaporation followed by drying under vacuum at 80° C.

In a variation, the ethylene oxide homopolymer can be replaced with a copolymer of ethylene oxide and allylglycidylether (5% molar) to which are added 1% by weight of Irgacure 651®. The solution in acetonitrile is spreaded on a polypropylene support to form a film of a thickness of 20 microns after drying. Under argon sweeping, the film is submitted to UV rays produced by a Hanovia® type lamp having its maximum of emission at 254 nm. The illumination corresponds to an energy of 130 mWcm$^{-2}$. The polymer cross-links through a radicalar process by the unsaturated segments and shows excellent elastomeric-type mechanical properties. Ternary mixtures molten salt/lithium salt/polymer can be obtained in a similar manner with, as the macromolecular material, acrylonitrile; polyvinylidene fluoride and its copolymers with hexafluoropropene, in particular those soluble acetone and easily embodied; or methyl polymethacrylate.

EXAMPLE 17

A polymer electrolyte is prepared by polymerisation in situ of a mixture of the monomer of Example 11 (25% by weight), lithium bis-trifluoromethanesulfonimidide (24%) and the molten salt of Example 1 (45%), and 1% of the radical initiator

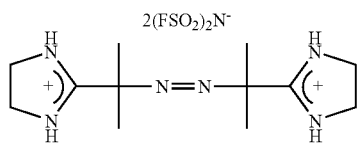

This initiator is obtained by exchange in water from the commercial chloride (Wako) and K(FSO$_2$)$_2$N). The liquid mixture is spreaded in the form of a film of a thickness of 30 microns on a polypropylene support, and polymerized in a tunnel oven under nitrogen atmosphere at 80° C. for 1 hour. The electrolyte thus obtained is an elastomer having an anodic stability domain higher than 5V and a conductivity greater than $3 \times 10^{-4}$ Scm$^{-1}$ at 25° C.

EXAMPLE 18

A secondary electrochemical generator is manufactured with a double oxide of cobalt and lithium LiCoO$_2$ as the active material for the positive electrode, and titanium and lithium spinel Li$_4$Ti$_5$O$_{12}$ as the active material for the negative electrode. The electrolyte is prepared according to Example 14 in the form of a 25 microns film. Each electrode of the composite type is prepared by spreading a suspension of the active material carbon black (Ketjenblack®) in a solution of a copolymer ethylene-copropylenediene (Aldrich) in cyclohexane. The final composition corresponds to 90% by volume of active material, 5% v/v of carbon black and 5% of copolymer. After spreading on aluminium current collectors of a thickness of 8 microns, the negative electrode contains 16.4 mg of active material per cm$^2$, (2.9 mAhcm$^{-2}$), and the positive electrode 16.5 mg of active material per cm$^2$, (2.7 mAhcm$^{-2}$). The electrodes and the current collectors are cut in squares of 4 cm$^2$ and placed on each side of a microporous polyethylene membrane (Celgard®) wetted with the liquid electrolyte prepared in Example 14. The battery thus assembled is characterized by slow voltammetry with a MacPile® type apparatus (Claix France). 92% of the capacity of the positive electrode is obtained in the voltage domain 2-2.8 V at a sweeping speed of 10 mV.mn$^{-1}$. The energy density in this configuration is 85 Wh.kg$^{-1}$.

EXAMPLE 19

A secondary electrochemical generator is manufactured with the double phosphate of iron-doped manganese and lithium LiMn$_{0.9}$Fe$_{0.1}$PO$_4$, as the active material of the positive electrode, and titanium and lithium spinel Li$_4$Ti$_5$O$_{12}$ as the active material for the negative electrode. The electrolyte is prepared according to Example 15 in the form of a film of a thickness of 25 microns. Each electrode of the composite type is prepared by spreading a suspension of 45% by volume of the active material, 5% v/v of carbon black (Ketjenblack®) and a solution of the components of the electrolyte according to Example 12 (50% v/v) in acetonitrile. The aluminium current collectors have a thickness of 8 microns. The positive electrode collector is covered with a protective coating of graphite (Acheson). After spreading, the negative electrode has a charge of 12 mg of active material per cm$^2$ (2.2 mAhcm$^{-2}$) and the positive electrode 14 mg of active material per cm$^2$ (2.4 mAhcm$^{-2}$). The electrodes and the current collectors are cut in squares of 4 cm$^2$ and placed on each side of the electrolyte and the assembly is laminated at 80° C. to ensure a good contact at the interfaces. The battery thus assembled is characterized by slow voltammetry. 82% of the capacity of the positive electrode are obtained in the voltage domain 2.6-3.2 V at a sweeping speed of 10 mV.mn$^{-1}$. The energy density in this configuration is close to 100 Wh.kg$^{-1}$.

EXAMPLE 20

A supercapacity is obtained from electrodes of activated carbon fibers of 900 m$^2$ g$^{-1}$ (Spectracarb®). Two squares of 4 cm$^2$ are cut in the carbon fabric and wetted under vaccum with the electrolyte prepared in Example 1. Both symmetrical electrodes are separated with a porous polyethylene membrane (Celgard®) wetted under vacuum by the same ionic liquid. Both collectors of current are in aluminium of 10 μm coated by cathodic spraying of protective layer of 5000 Å of molybdenum. The volumic capacity for a maximum charge tension of 2.8 V is 12 Fcm$^{-3}$, (3 Wh.L$^{-1}$) at the threshold tension cut of 1.2 V.

EXAMPLE 21

The imidazolium salt of Example 1 is used as a solvent of yttrium bis-trifluoromethanesulfonimidide in concentration of 0.1M. This liquid is used as a catalyst in a Diels-Alder reaction of cyclopentadiene with methyl acrylate. The reagents are mixed in stoichiometric quantities, and 30% v/v of the ionic liquid are added. Under agitation, the reaction is completed in 1 hour at 25° C. The reaction products are extracted with hexane, which is non-miscible with the ionic compound. The ratio endo/exo is 9:1. The catalyst treated at 100° C. under vacuum can be reused without loss of activity.

EXAMPLE 22

The molten salt prepared in Example 12 is used as a solvent for nucleophilic substitution reactions. 10 g of that salt and 3 g of potassium cyanide are put in a glass tube in an oven and the temperature is raised to 250° C. 4 g of benzyl chloride are heated at 60° C. for 2 hours. The yield of conversion of the benzyl chloride into benzyl cyanide is 85%. The molten salt can be easily recycled by washing with water and evaporation.

While the invention has been described in connection with specific embodiments thereof, it will be understood that it is capable of further modifications, and this application is intended to cover any variations, uses or adaptations of the invention following, in general, the principles of the invention, and including such departures from the present description as come within known or customary practice within the art to which the invention pertains, and as may be applied to the essential features hereinbefore set forth, and as follows in the scope of the appended claims.

What is claimed is:

1. A medium for chemical or electrochemical reactions involving soluble species present in said medium, comprising:

at least one ionic compound comprising a cation of the onium type having at least one heteroatom selected from the group consisting of N, O, S and P carrying a positive charge; and an anion including, in whole or in part, at least one imide ion of the type (FX$_1$O)N—(OX$_2$F) wherein X$_1$ and X$_2$ are the same or different and comprise SO or PF, wherein the cation comprises a compound selected from the group consisting of:

a) a compound of the formula:

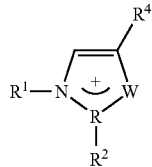

wherein W is O, S or N;
wherein $R^1$ and $R^4$ are the same or different and represent H, alkyl alkenyl, oxaalkyl, oxaalkenyl azaalkyl, azaalkenyl, thiaalkyl, thiaalkenyl, dialkylazo, cyclic or heterocyclic aliphatic radicals of from 4 to 26 carbon atoms, or groups comprising several aromatic or heterocyclic nuclei; and
wherein $R^2$ represents $R^1$, $R^1O-$, $(R^1)^2N-$, or $R^1S-$;

b) a compound of the formula:

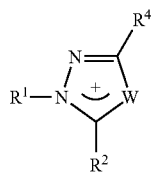

wherein W is O, S or N;
wherein $R^1$ and $R^4$ are the same or different and represent H, alkyl, alkenyl, oxaalkyl, oxaalkenyl, azaalkyl, azaalkenyl, thiaalky thiaalkenyl, dialkylazo, cyclic or heterocyclic aliphatic radicals of from 4 to 26 carbon atoms, or groups comprising several aromatic or heterocyclic nuclei; and
wherein $R^2$ represents $R^1$, $R^1O-$, $(R^1)_2N-$, or $R^1S-$;

c) a compound of the formula:

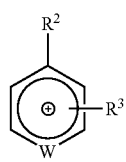

wherein W is O, S or N;
wherein $R^1$ and $R^3$ are the same or different and represent H, alkyl, alkenyl, oxaalkyl, oxaalkenyl, azaalkyl, azaalkenyl, thiaalkyl, thiaallcenyl, dialkylazo, cyclic or heterocyclic aliphatic radicals of from 4 to 26 carbon atoms, or groups comprising several aromatic or heterocyclic nuclei; and
wherein $R^2$ represents $R^1$, $R^1O-$, $(R^1)_2N-$, or $R^1S-$;

d) a compound of the formula:

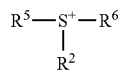

wherein $R^1$ represents H, alkyl, alkenyl, oxaalkyl, oxaalkenyl, azaalkyl, azaalkenyl, thiaalkyl, thiaalkenyl, dialkylazo, cyclic or a heterocyclic aliphatic radical of from 4 to 26 carbon atoms, or a group comprising several aromatic or heterocyclic nuclei; and
wherein $R^2$, $R^5$ and $R^6$ are the same or different and represent $R^1$, $R^1O-$, $(R^1)_2N-$, or $R^1S-$;

e) a compound of the formula:

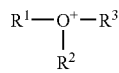

wherein $R^1$ and $R^3$ are the same or different and represent H, alkyl, alkenyl, oxaalky oxaalkenyl, azaalkyl, azaallkenyl, thiaalkenyl, dialkylazo, cyclic or a heterocyclic aliphatic radicals of from 4 to 26 carbon atoms, or groups comprising several aromatic or heterocyclic nuclei; and
wherein $R^2$ represents $R^1$, $R^1O-$, $(R^1)_2N-$, or $R^1S-$; and f) a compound of the formula:

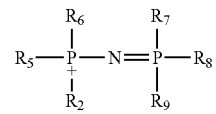

wherein $R^1$ represents H, alkyl, alkenyl, oxaaalkyl, oxaalkenyl, azaalkyl, azaalkenyl, thiaalkyl, thiaalkenyl, dialkylazo, cyclic or a heterocyclic aliphatic radical of from 4 to 26 carbon atoms, or a group comprising several aromatic or heterocyclic nuclei; and
wherein $R^2$ and $R^5$ to $R^9$ are the same or different and represent $R^1$, $R^1O-$, $(R^1)_2N-$, or $R^1S-$.

2. The medium according to claim 1, wherein the medium is in combination with at least one other component selected from the group consisting of a metallic salt, a polar polymer, and an aprotic cosolvent.

3. The medium according to claim 1, wherein the medium is non-flammable.

4. The medium according to claim 1, wherein the ionic compound is molten.

5. The medium according to claim 4, wherein the ionic compound is a solvent.

6. The medium according to claim 5, wherein catalyst is dissolved in the solvent.

7. The medium according to claim 6, wherein the catalyst comprises a bipyridine, a porphyrine, a phosphine, an arsine or a metallocene.

8. The medium according to claim 1, further comprising the soluble species dissolved in the medium.

* * * * *